United States Patent
Nguyen

[19]

[11] Patent Number: 5,947,485
[45] Date of Patent: Sep. 7, 1999

[54] COLLET ASSEMBLY AND MANUFACTURING PROCESS

[76] Inventor: Tuan Nguyen, 9052 Blair River Cir., Fountain Valley, Calif. 92708

[21] Appl. No.: 08/893,273

[22] Filed: Jul. 15, 1997

[51] Int. Cl.$^6$ .............................. B23B 29/04; B23B 29/14
[52] U.S. Cl. ......................... 279/46.2; 279/43.1; 279/47; 279/51; 279/58; 409/231; 409/232; 433/114; 433/132
[58] Field of Search .................. 279/46.2, 43.1, 279/51, 47, 58; 409/231, 232; 433/114, 132

[56] References Cited

U.S. PATENT DOCUMENTS

| | | | |
|---|---|---|---|
| 2,346,706 | 5/1944 | Stoner | 279/46 |
| 3,035,845 | 11/1962 | Benjamin | 279/47 |

*Primary Examiner*—Daniel W. Howell
*Assistant Examiner*—Mark T. Henderson
*Attorney, Agent, or Firm*—Steins & Associates

[57] ABSTRACT

An Improved Collet Assembly and Manufacturing Process is disclosed. Also disclosed is an improved collet that includes a spindle, a center portion comprising several tabs and a collar. The disclosed collet is manufactured from a single piece of stock, and as such, that the tabs are formed from this unitary piece. The disclosed collet is inserted into a collet housing that is further defined by a bore in its center. The preferred collet housing bore is further defined by a sloped portion that cooperates with the tabs formed on the collet to restrain a burr shaft from rotational or axial movement. The collet assembly of the present invention provides improved balance and therefore wear properties over previous collet assembly. In particular, the disclosed collet assembly is well suited for application inside a cannister assembly of a air-powered dental tool handpiece.

6 Claims, 7 Drawing Sheets

COLLET ASSEMBLY AND MANUFACTURING PROCESS

BACKGROUND OF THE INVENTION

1. Field of the Invention

This invention relates generally to collets or chucks for grasping rotating tool bit shafts and, more specifically, to an Improved Collet Assembly and Manufacturing Process.

2. Description of Related Art

FIG. 1 is a perspective view of a conventional dental handpiece 10 within which the device of the present invention might be used. Dental handpieces 10 are used to operate "burrs", or rotating cutting tools, similar to conventional drill or router bits, for cutting or grinding teeth or dental appliances. The typical handpiece 10 is designed to receive compressed air for its operation from a dentist's chair. These handpieces 10 are available in a variety of shapes and sizes, depending upon their purpose and/or application. As depicted, the handpiece 10 comprises a handle 12 and a head 14. A "canister assembly" is housed within the head 14. The "canister assembly" comprises, essentially, a compressed air-powered motor with a removable tool shaft 16 held therein. The tool shaft 16 in a typical handpiece 10 is removable so that different burrs or bits may be used so long as they have the same size tool shaft 16. The tool shaft 16 is held within the canister assembly by the "collet assembly".

FIG. 1a depicts a typical prior art collet assembly 60. The state of the prior art collet for dental handpieces comprises a tapered portion 62 that further has an axial bore 64 drilled into it that is configured to receive a burr or bit. The burr or bit is held in place by a pair of free-floating wedges 66 that ride in slots 68 formed around the circumference of the tapered portion 62. Once a burr or bit is inserted into this prior collet 60, the wedges 66 are biased towards the shaft to hold the shaft in place both axially and rotationally.

There are at two least problems with this prior collet design. First, there are significant manufacturing difficulties in this design. Since the typical burr or bit is approximately 0.06 inches in diameter, the wedges and slots must be extremely small—on the order of 0.01 inches wide and 0.1 inches long. Because of the high speed of rotation of the shaft in operation, the shaft must be balanced to high precision. This, in turn necessitates extremely tight tolerances for the wedges and slots. While these tolerances are attainable, it adds considerable cost to the manufacturing process. What is needed is a collet that is precision balanced, but does not require extraordinarily tight manufacturing tolerances.

The second deficiency with the prior design as shown in FIG. 1a is the lack of self-centering capability. Because the collet is fairly thin-walled, there is a limit to the number of slots that can be cut through it before its structural integrity is compromised. The prior collet, therefore, can only have the two slots and wedges. The problem with only having two wedges is that the burr or bit is not automatically centered by the collet. As stated above, the high rotational speed of the collet means that any slight misalignment will result in a short service life for the canister and collet (due to wear). What is needed is an improved collet that self-centers the shaft held therein.

SUMMARY OF THE INVENTION

In light of the aforementioned problems associated with the prior devices, it is an object of the present invention to provide an Improved Collet Assembly and Manufacturing Process. It is a further object that the improved collet of the present invention include a spindle, a center portion comprising several tabs and a collar. It is an object that the collet be manufactured from a single piece of stock, and as such, that the tabs are formed from this unitary piece. The collet is inserted into a collet housing that is further defined by a bore in its center. It is an object of this invention that the collet housing bore is further defined by a sloped portion that cooperates with the tabs formed on the collet to restrain a burr shaft from rotational or axial movement. It is a still further object that the collet assembly of the present invention provide improved balance and therefore wear properties over previous collet assembly.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an Improved Collet Assembly and Manufacturing Process.

Figure 1:
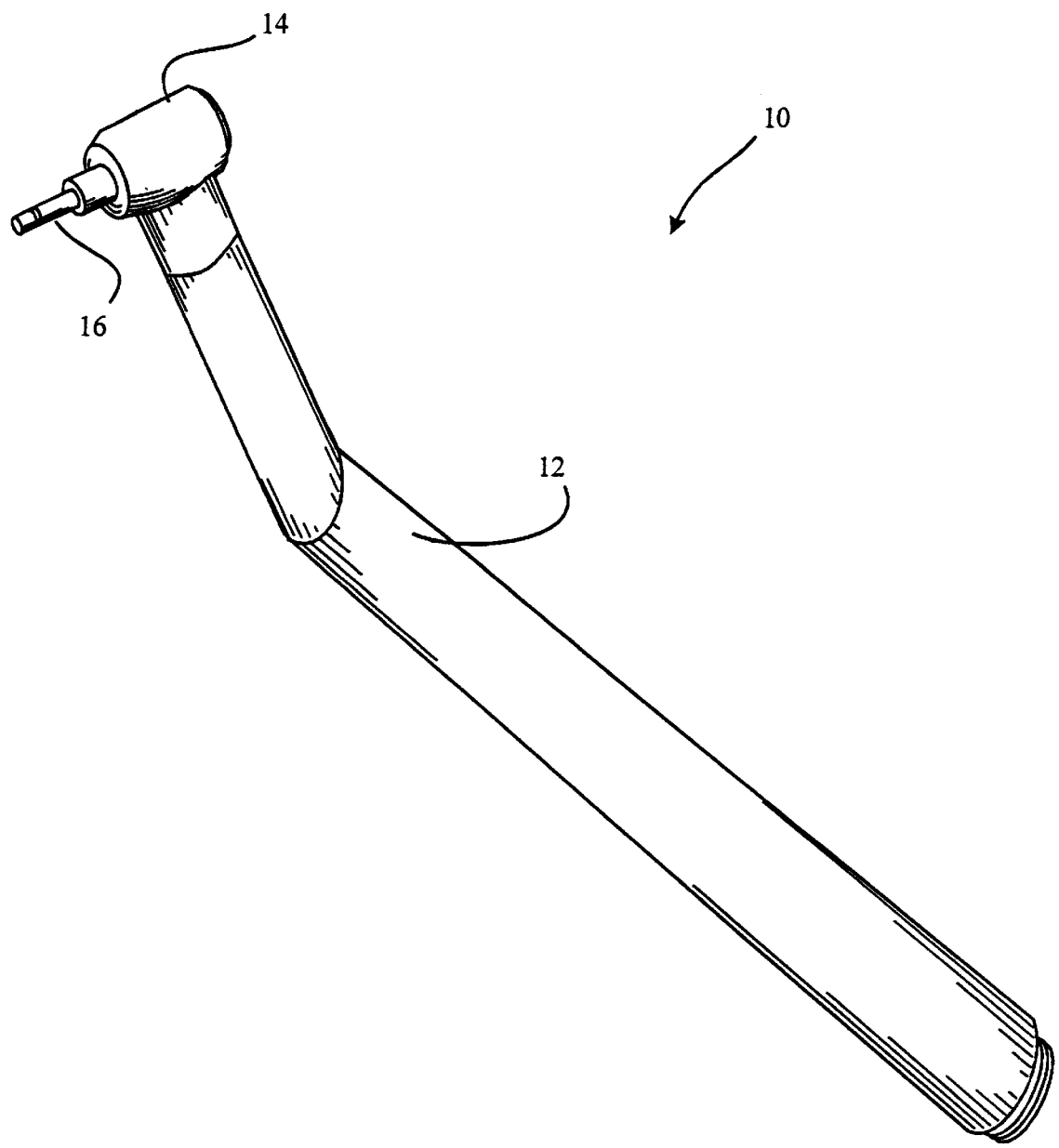
FIG. 1 is a perspective view of a dental handpiece.
Figure 1A:
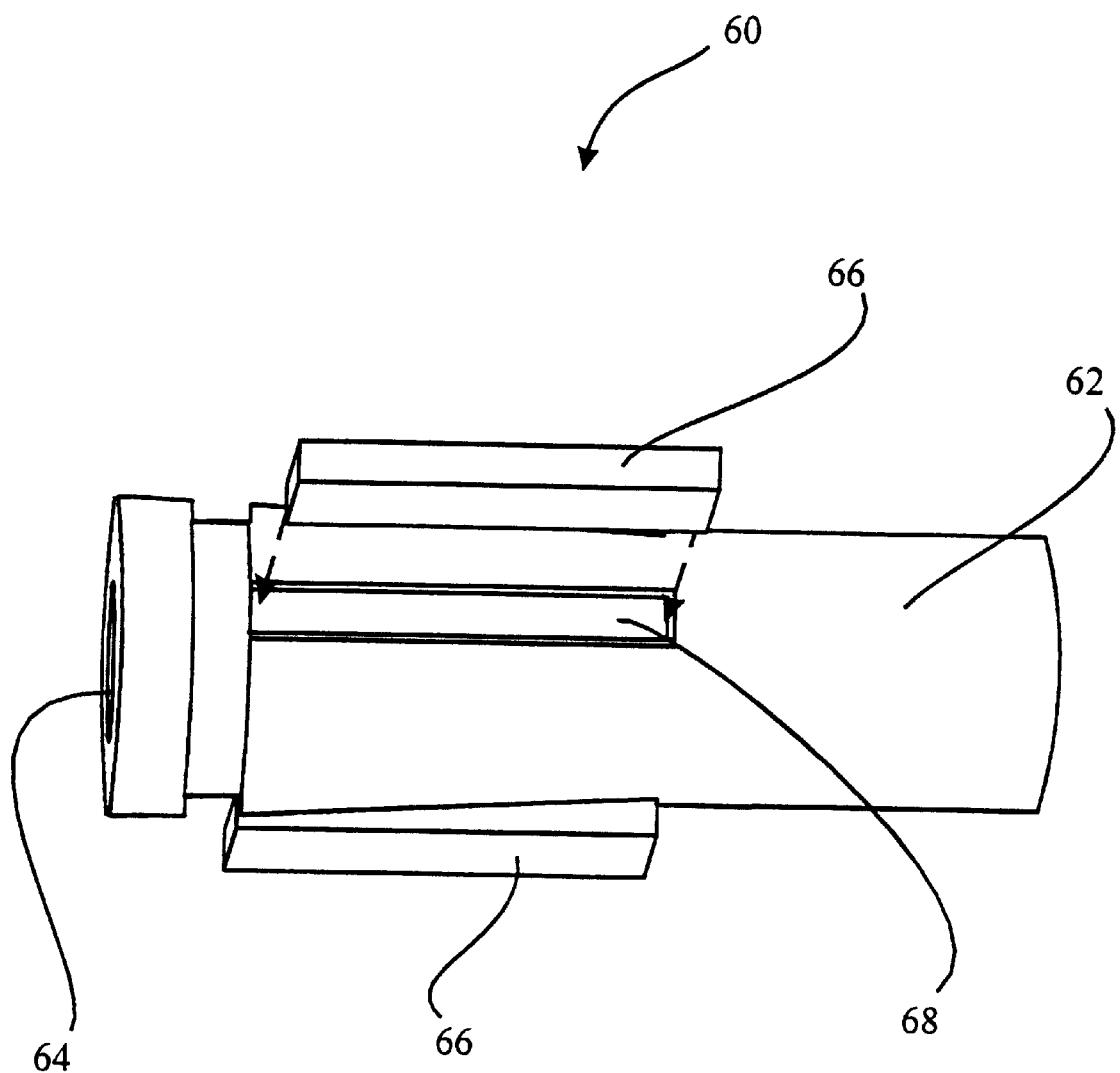
FIG. 1a is a perspective view of a typical prior collet assembly.
Figure 2:
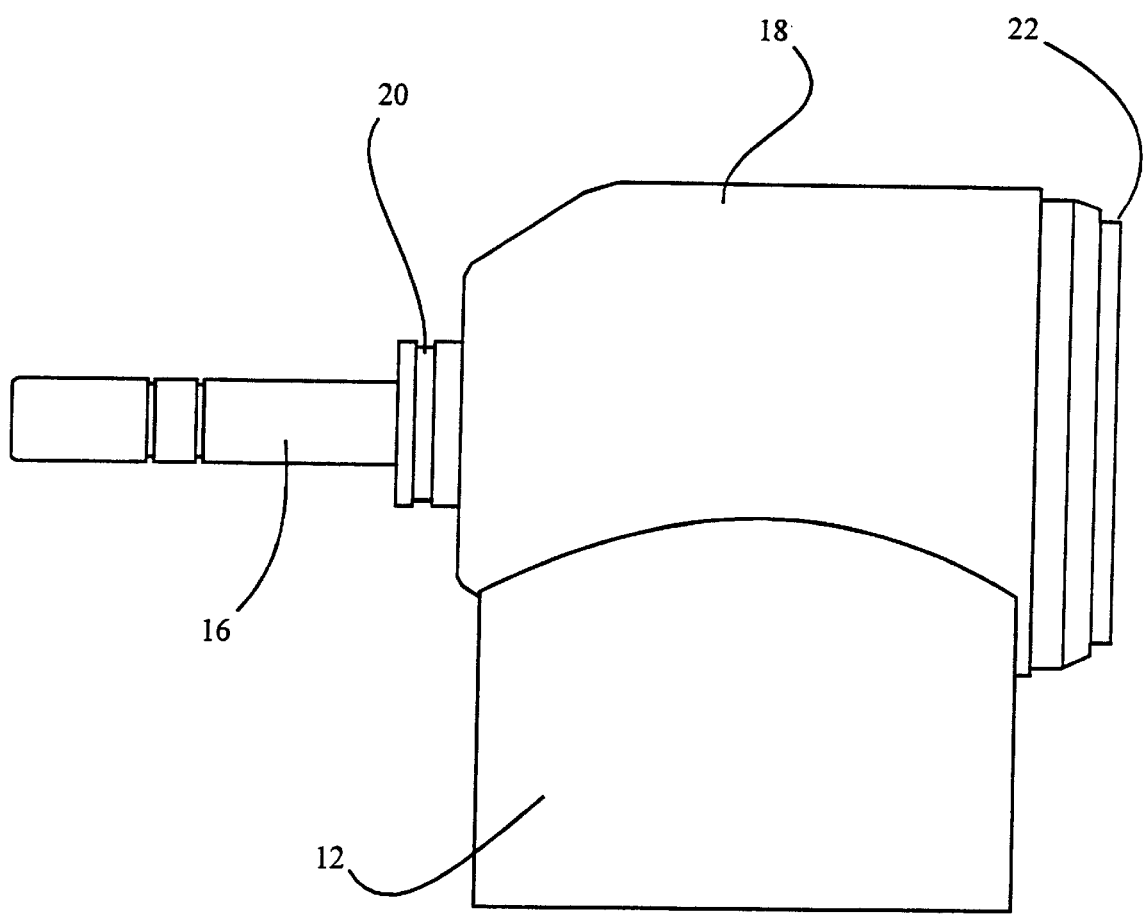
FIG. 2 is a side view of the head of a dental handpiece.

The present invention can best be understood by initial consideration of FIG. 2. FIG. 2 is a side view of the head 18 of a dental handpiece (see FIG. 1). The head 18 houses, among other things, the collet assembly 20. The collet assembly 20 is configured to accept a tool shaft 16 and restrain it from rotational or axial motion with respect to the collet assembly 20. In order to remove the tool shaft 16, one need simply press on the release button 22 and pull axially (away from the collet assembly 20) on the tool shaft 16.

Figure 3:
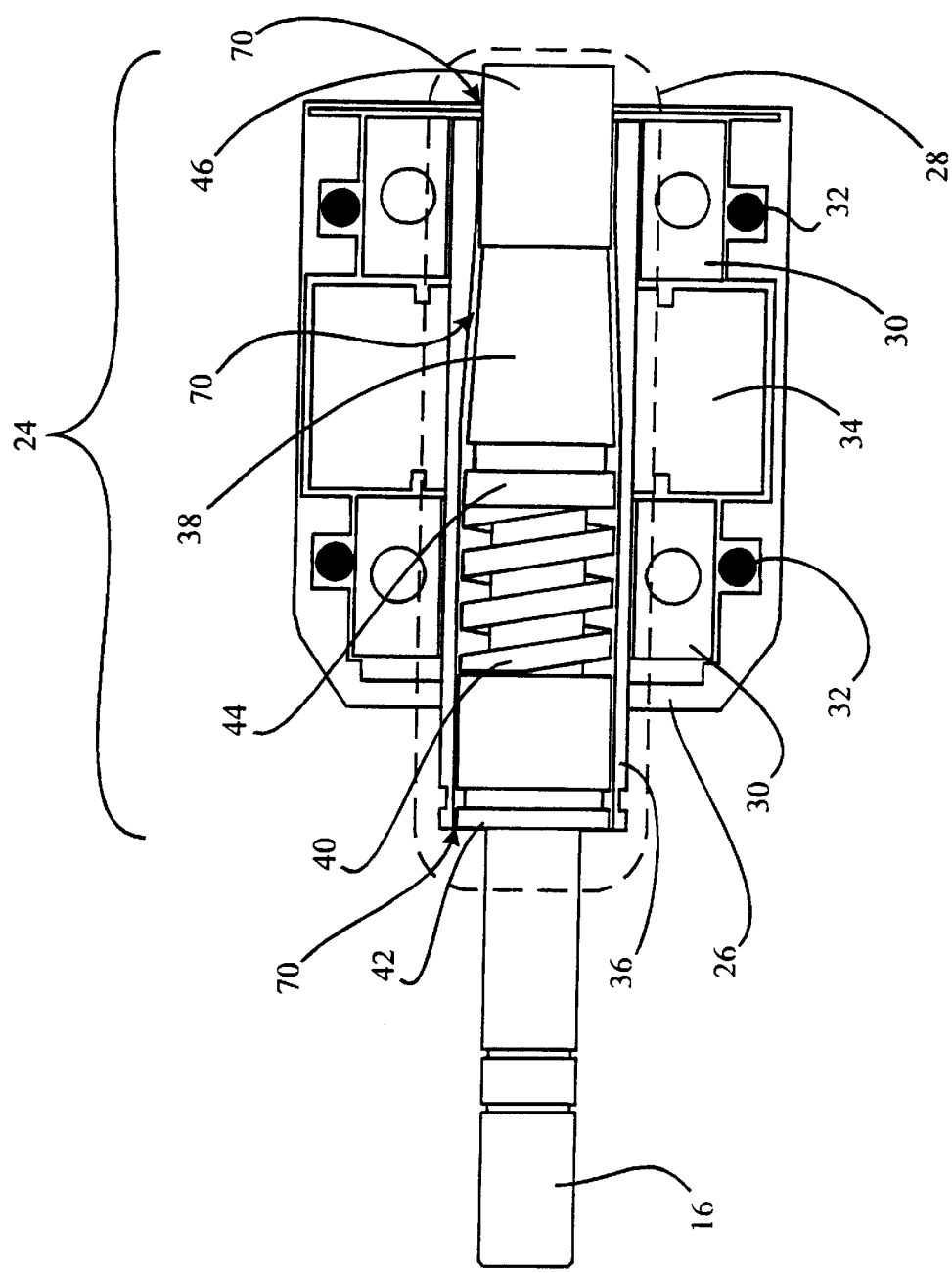
FIG. 3 is a cutaway side view of a preferred canister assembly of the present invention.

Now turning to FIG. 3, one may better understand the unique attributes of the present invention. FIG. 3 is a cutaway side view of a preferred canister assembly 24 of the present invention. The canister assembly 24 typically is inserted into the head after first unscrewing the release button (see FIG. 2). The canister assembly 24 comprises a canister housing 26 within which the collet assembly 28 rotates. The collet assembly 28 rotates on a pair of bearing assemblies 30 that are typically pressed onto the collet assembly 28 and then are each sealed to the canister housing 26 by an O-ring 32. These bearing assemblies 30 and O-rings 32 are in use in conventional canister assemblies. The collet assembly 28 is caused to rotate when compressed air is directed across the turbine 34. The turbine 34 is simply a single-stage fan in its function. As describe above, the tool shaft 16 is held in the collet assembly 28, and therefore will rotate with the collet assembly 28.

The unique collet assembly 28 of the present invention comprises a collet housing 36, though which is an axial housing bore 70, within which is a collet 38, a spring 40 and a retainer 42. The collet 38 is further defined by a collar 44 at its front end, and a spindle 46 at its rear end. The tool shaft 16 slides into the collet 38 through the collar 44, and is held in the collet 38 by the interference fit between the shaft 16 and the collet 38; further detail regarding this situation is found below in connection with FIGS. 4–7. The collet 38 is urged against the collet housing 36 as a result of the spring 40 pressing against the collar 44. If sufficient axial force is applied to the spindle 46 to oppose the spring 40, the collet 38 will no longer be in contact with the collet housing 36. This axial force is provided by a user pressing on the release button (see FIG. 2), which in turn will contact the spindle. The spring 40 and collet 38 are retained within the collet housing 36 by the retainer 42. The retainer 42 is attached to the collet housing 36, preferably via an interference fit. The materials of construction of all of these elements (with the exception of the O-rings) is metal, as is well known in the art.

Figure 4:
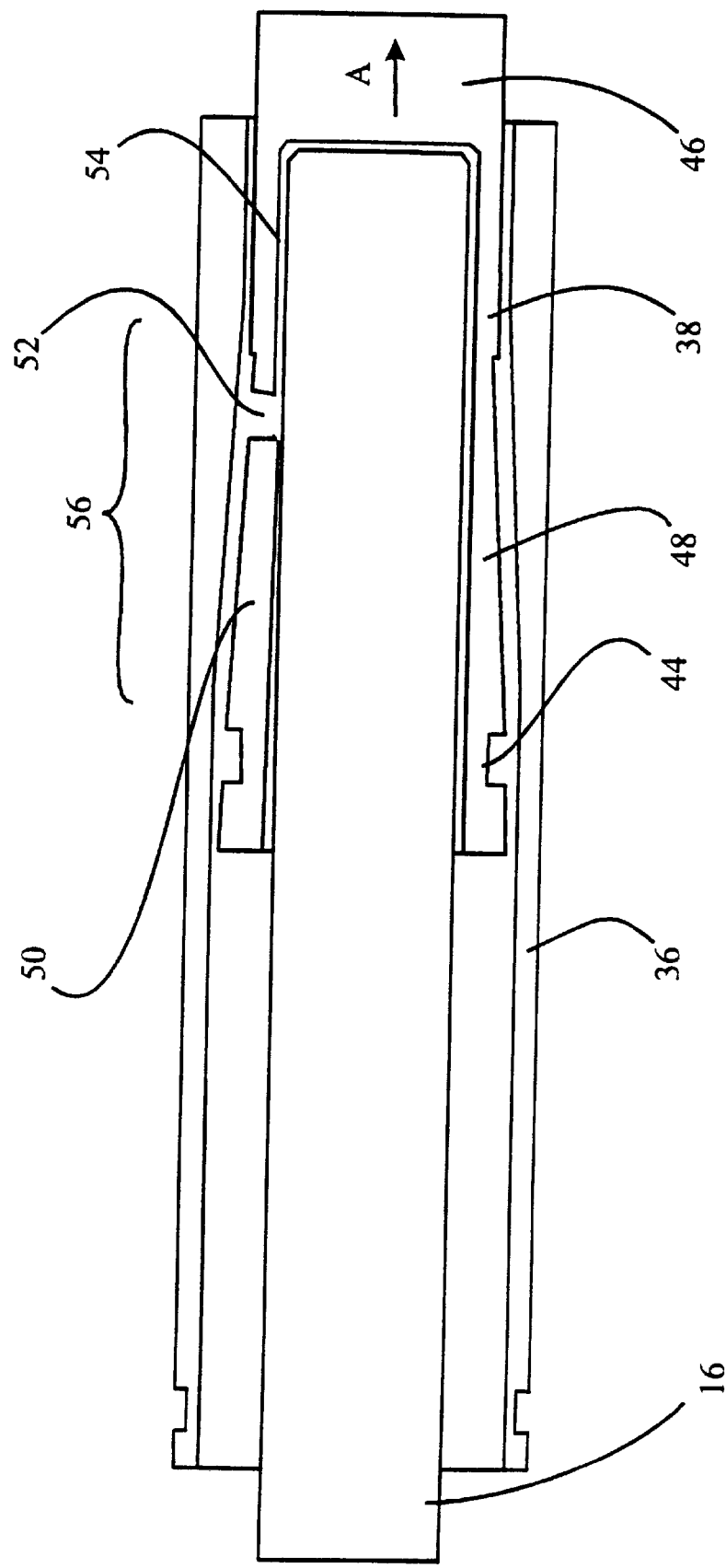
FIG. 4 is a partial cutaway side view of a preferred collet assembly of the present invention.

FIG. 4 provides illumination regarding the unique collet design and the process for making it. FIG. 4 is a partial cutaway side view of a preferred collet assembly of the present invention. As can be seen, the collet 38 comprises a spindle 46 and a collar 44, which are connected to one another by a plurality of struts 48 (only one shown here). The collet 38 also comprises a plurality of tabs 50 (only one is shown), that are separated from the spindle 46 by a aperture 52. The collar 44, tabs 50, struts 48 and spindle 46 form a bore 54 in the center of the collet 38. It should be noticed that the collet housing 36 is defined by a tapered portion 56 on its interior surface that is configured to interact with the tabs 50. It should further be noticed that the tabs 50 are thicker than the struts 48, and as such, will contact the tapered portion 56 before the struts 48, as the collet 38 is moved in direction "A".

Once the tool shaft 16 is inserted into the bore 54, the collet 38 is biased rearwardly in the direction of arrow "A" (see spring discussion above) until the tabs 50 are pressed against the tool shaft 16 by the tapered portion 56 of the housing. If the collet 38 is moved in the direction opposite arrow "A", the interference forces between the tapered portion 56, the tabs 50, and the tool shaft 16 will be removed, and the tool shaft 16 will slip easily out of the bore 54.

A discussion of the unique process to manufacture this unique collet is now in order. First, a piece of solid metal stock is machined to have the outer surface shape and dimensions of the collet 38 depicted in FIGS. 3 and 4. A hole, having a diameter smaller than that of the tool shaft 16 is drilled through the center of the piece from the collar 44 to the spindle 46. The apertures 52 and slots (see FIGS. 6 and 7) are then cut to free the tabs 50 from the struts 48. Next, the hole is reamed out to the final diameter that will permit the tool shaft 16 to be inserted. Since the tabs 50 were free-floating when the hole was reamed out, they will not be reamed (or made thinner) during this boring step, but will simply deflect out of the way of the cutting tool. The result is a simple, tight tolerance, low-cost method for creating these tabs 50 that are thicker than the struts 48, in a collet 38 formed in a unitary piece.

Figure 5:
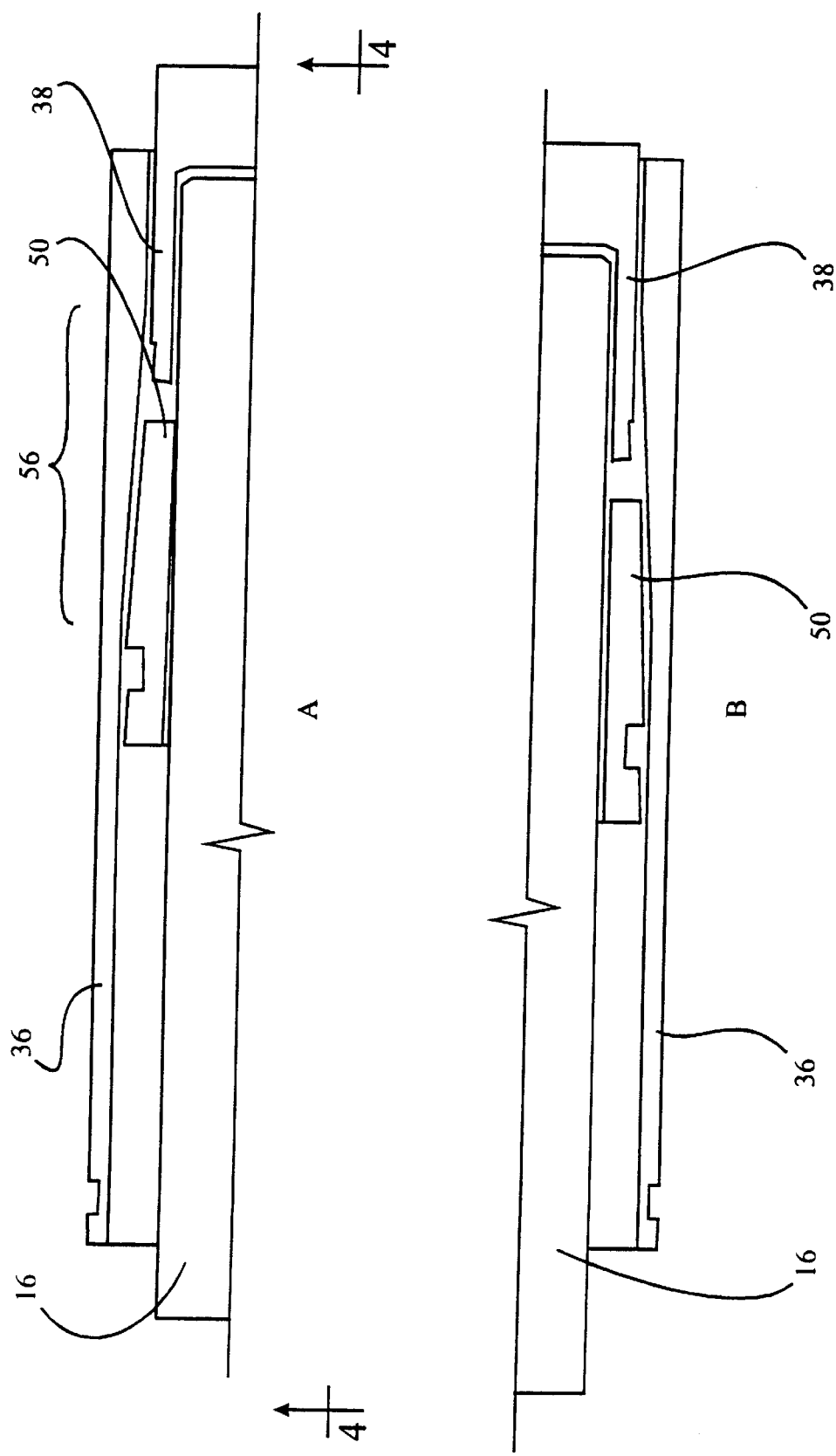
FIG. 5 is a pair of partial cutaway side views of the collet assembly of FIG. 4, depicting the restraining action of the preferred tab.

FIG. 5 gives another depiction of the operation of the present invention. FIG. 5 is a pair of partial cutaway side views of the collet assembly of FIG. 4, depicting the restraining action of the preferred tabs 50. View A depicts the tool shaft 16 in a restrained condition inside of the collet 38. As is depicted, the tab 50 is being forced against the tool shaft 16 by the tapered portion 56 of the collet housing 36. View B depicts the tool shaft 16 in an un-restrained condition inside of the collet 38. As can be seen, the collet 38 has moved to the left in the diagram, and the tab 50 has become disengaged from the collet housing 36, thereby releasing the tool shaft 16 to be removed.

Figure 6:
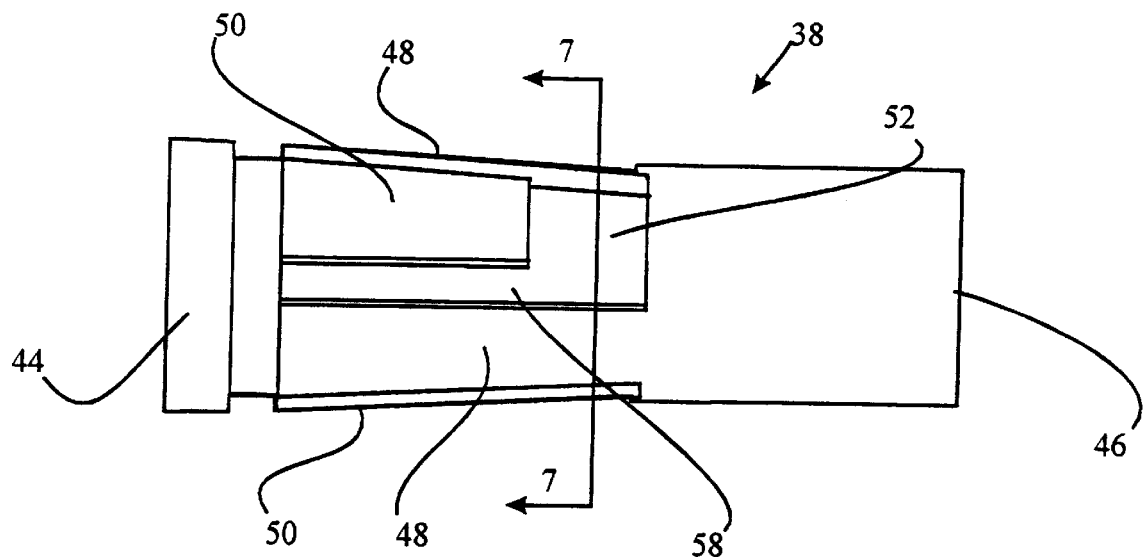
FIG. 6 is a side view of a preferred collet.

Now turning to FIG. 6, we can gain an even better understanding of the improved collet 38 of the present invention. FIG. 6 is a side view of a preferred collet 38. The collet 38 is preferably cylindrical in shape, and is defined by a plurality of tabs 50 and struts 48. Between each tab 50 and strut 48 is a slot 58 that connects to the bore (not shown) and separates each strut 48 from the adjacent tabs 50. Each tab 50 is further separated at one end from the spindle 46 by an aperture 52, and as such, the tabs 50 are free to deflect outwardly and inwardly, as necessary.

Figure 7:
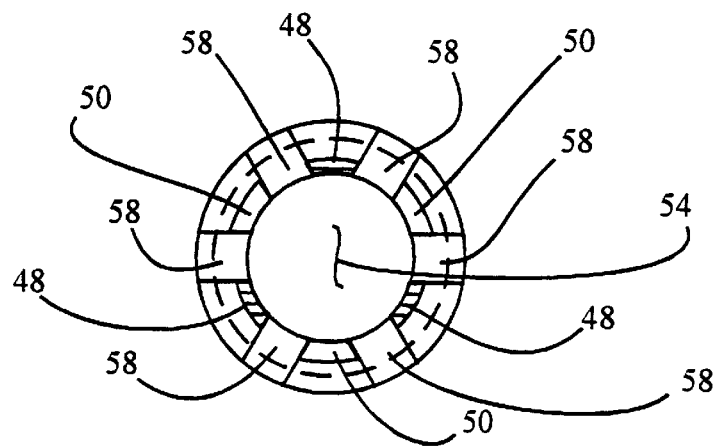
FIG. 7 is a partial cutaway side view of the collet of FIG. 6, depicting the preferred cross-section of the collet.

FIG. 7 is presented to provide further detail regarding the collet 38. FIG. 7 is a partial cutaway side view of the collet 38 of FIG. 6, depicting the preferred cross-section of the collet along the line A—A. In the depicted embodiment, there are three struts 48, separated from the three tabs 50 by six slots 58 that penetrate from the outer surface of the collet 38 to the inner bore 54. In the depicted form, there will be an even and balanced (three-sided) force against the tool shaft (see previous figures) by the tabs 50. This balanced force will also cause the tool shaft to be self-centered, without the need for the special manufacturing tolerances of the prior devices. These design characteristics result in well-balanced rotation.

In its preferred form, the present canister assembly 24 will sustain a collet assembly 28 rotational velocity of 510 to 530 revolutions per minute, as compared to 460 RPM for a conventional unit. Furthermore, the balanced design and easy repeatability has resulted in twice the longevity of the conventional canister assembly 24.

One should understand that while the present embodiment depicts a "rear-release" collet, the present unique collet design is easily reconfigured to permit pressure on the front of the collet to release the shaft. The rear-release collet is a necessity for the dental handpiece application to prevent blood and other foreign matter from entering the open end of the collet and thereby causing the tool shaft to be jammed therein.

It should furthermore be appreciated that the present invention is readily adaptable to hold any diameter of burr or bit, if desired. In other words, a larger version of the same collet assembly would function identically to that previously-described, and with the same advantages. The difference is simply one of scale.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved collet assembly for holding a tool shaft, comprising:

a collet defined by an axial collet bore adapted to receive said shaft, and a plurality of tabs integral to said collet and adjacent to said bore;

a collet housing including an axial housing bore adapted to receive said collet and further including a tapered portion, whereby said tabs cooperate with said tapered portion to hold said tool shaft; and further comprising biasing means for biasing said tabs towards said tapered portion, said biasing means comprising a spring.

2. The collet assembly of claim 1, wherein:

said collet comprises:

a spindle;

a center portion extending from said spindle and comprising said tabs; and a collar adjacent to said center portion; and wherein said axial collet bore penetrates said collar and said center portion.

3. The collet assembly of claim 2, wherein said center portion further comprises a plurality of struts extending between said spindle and said collar.

4. The collet assembly of claim 1, wherein said biasing means exerts biasing force at said collar.

5. The collet assembly of claim 4, wherein:

said collet housing further comprises a first end and a second end, with said axial housing bore extending from said first end to said second end;

said collet assembly further comprises a retainer attached in said housing bore between said first end and said biasing means; and said spindle extends out of said second end.

6. The collet assembly of claim 5, wherein said collet comprises a unitary piece.

* * * * *